(12) United States Patent
Foster et al.

(10) Patent No.: US 7,822,486 B2
(45) Date of Patent: Oct. 26, 2010

(54) CUSTOM SIZED NEURAL ELECTRODES

(75) Inventors: Arthur J. Foster, Centerville, MN (US); Brian J. Erickson, Woodbury, MN (US); Michael D. Bierk, St. Paul, MN (US)

(73) Assignee: EnteroMedics Inc., St. Paul, MN (US)

( * ) Notice: Subject to any disclaimer, the term of this patent is extended or adjusted under 35 U.S.C. 154(b) by 697 days.

(21) Appl. No.: 11/205,962

(22) Filed: Aug. 17, 2005

(65) Prior Publication Data

US 2007/0043411 A1    Feb. 22, 2007

(51) Int. Cl.
*A61N 1/05* (2006.01)
(52) U.S. Cl. .................................... 607/118
(58) Field of Classification Search ............ 607/118, 607/40, 2, 113, 149, 46, 150, 63; 600/377
See application file for complete search history.

(56) References Cited

U.S. PATENT DOCUMENTS

| | | | |
|---|---|---|---|
| 3,128,760 A | 4/1964 | Baker | |
| 3,411,507 A | 11/1968 | Wingrove | |
| 4,114,625 A | 9/1978 | Onat | |
| 4,198,963 A | 4/1980 | Barkalow et al. | |
| 4,541,432 A | 9/1985 | Molina-Negro et al. | |
| 4,702,254 A | 10/1987 | Zabara | |
| 4,776,349 A | 10/1988 | Nashef et al. | |
| 4,867,164 A | 9/1989 | Zabara | |
| 4,934,368 A | 6/1990 | Lynch | |
| 4,979,511 A | 12/1990 | Terry, Jr. | |

(Continued)

FOREIGN PATENT DOCUMENTS

DE    198 47 446 A1    4/2000

(Continued)

OTHER PUBLICATIONS

George, et al., "Vagus nerve stimulation therapy," *Neurology*, vol. 59, Suppl. 4, pp. S56-61 (Sep. 2002).

(Continued)

*Primary Examiner*—George R Evanisko
*Assistant Examiner*—Michael D'Abreu
(74) *Attorney, Agent, or Firm*—Merchant & Gould P.C.

(57) ABSTRACT

An apparatus for applying a signal to a nerve for the treatment of a disorder includes a main electrode body of biocompatible dielectric material and having a concave upper surface and an opposite lower surface. The concave upper surface curves about an axis and has a curvature sized to receive a nerve within the concave surface with an axis of the nerve substantially parallel to an axis of the concave surface. An electrode contact of electrically conductive material is secured to the main electrode body and has an electrode contact surface exposed on the concave surface. The concave surface terminates at opposite first and second upper ends. The electrode contact has a first end near the first end of the concave surface. A secondary electrode body of biocompatible dielectric material is attached to the first upper end of the concave surface. An electrode lead has an electrical conductor surrounded by a biocompatible insulative coating with both the conductor and the coating flexible relative to a longitudinal axis of the lead. A first end of the lead is secured to the secondary electrode body and with a first end of said conductor electrically connected to said first end of said electrode contact.

6 Claims, 4 Drawing Sheets

U.S. PATENT DOCUMENTS

Figure 6:
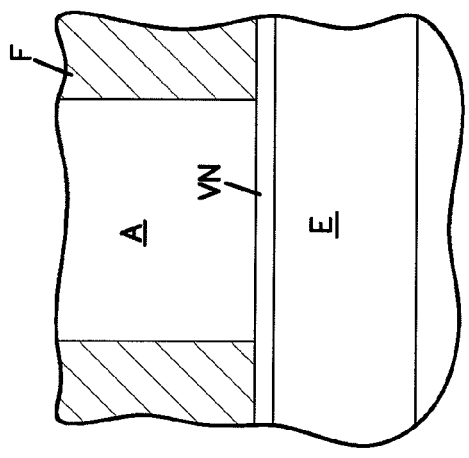

| | | |
|---|---|---|
| 5,025,807 A | 6/1991 | Zabara |
| 5,188,104 A | 2/1993 | Wernicke et al. |
| 5,199,430 A | 4/1993 | Fang et al. |
| 5,215,089 A | 6/1993 | Baker, Jr. |
| 5,226,429 A | 7/1993 | Kuzmak |
| 5,231,988 A | 8/1993 | Wernicke et al. |
| 5,251,634 A | 10/1993 | Weinberg |
| 5,263,480 A | 11/1993 | Wernicke et al. |
| 5,269,303 A | 12/1993 | Wernicke et al. |
| 5,292,344 A | 3/1994 | Douglas |
| 5,299,569 A | 4/1994 | Wernicke et al. |
| 5,330,515 A | 7/1994 | Rutecki et al. |
| 5,335,657 A | 8/1994 | Terry et al. |
| 5,344,438 A * | 9/1994 | Testerman et al. .......... 607/118 |
| 5,370,675 A | 12/1994 | Edwards et al. |
| 5,423,872 A | 6/1995 | Cigaina |
| 5,437,291 A | 8/1995 | Pasricha et al. |
| 5,514,175 A | 5/1996 | Kim et al. |
| 5,531,778 A * | 7/1996 | Maschino et al. .......... 607/118 |
| 5,540,730 A | 7/1996 | Terry et al. |
| 5,571,150 A | 11/1996 | Wernicke et al. |
| 5,601,604 A | 2/1997 | Vincent |
| 5,620,955 A | 4/1997 | Knight et al. |
| 5,690,691 A | 11/1997 | Chen et al. |
| 5,707,400 A | 1/1998 | Terry, Jr. et al. |
| 5,716,385 A | 2/1998 | Mittal et al. |
| 5,747,060 A | 5/1998 | Sackler |
| 5,749,907 A | 5/1998 | Mann |
| 5,830,434 A | 11/1998 | Taylor et al. |
| 5,836,994 A | 11/1998 | Bourgeois |
| 5,861,014 A | 1/1999 | Familoni |
| 5,919,216 A | 7/1999 | Houben et al. |
| 5,938,596 A * | 8/1999 | Woloszko et al. .......... 600/377 |
| 5,967,977 A | 10/1999 | Mullis et al. |
| 5,995,872 A | 11/1999 | Bourgeois |
| 6,083,249 A | 7/2000 | Familoni |
| 6,091,992 A | 7/2000 | Bourgeois et al. |
| 6,093,167 A | 7/2000 | Houben et al. |
| 6,097,984 A | 8/2000 | Douglas |
| 6,098,629 A | 8/2000 | Johnson et al. |
| 6,104,955 A | 8/2000 | Bourgeois |
| 6,111,715 A | 8/2000 | Tsuchiya et al. |
| 6,129,726 A | 10/2000 | Edwards |
| 6,135,978 A | 10/2000 | Houben et al. |
| 6,148,222 A | 11/2000 | Ramsey, III |
| 6,216,039 B1 | 4/2001 | Bourgeois |
| 6,238,423 B1 | 5/2001 | Bardy |
| 6,243,607 B1 | 6/2001 | Mintchev et al. |
| 6,261,280 B1 | 7/2001 | Houben et al. |
| 6,261,572 B1 | 7/2001 | Donovan |
| 6,290,961 B1 | 9/2001 | Aoki et al. |
| 6,292,703 B1 | 9/2001 | Meier et al. |
| 6,308,105 B1 | 10/2001 | Duysens et al. |
| 6,312,708 B1 | 11/2001 | Donovan |
| 6,341,236 B1 | 1/2002 | Osorio et al. |
| 6,364,899 B1 | 4/2002 | Dobak, III |
| 6,369,079 B1 | 4/2002 | Rubin et al. |
| 6,405,732 B1 | 6/2002 | Edwards et al. |
| 6,418,346 B1 | 7/2002 | Nelson et al. |
| 6,449,511 B1 | 9/2002 | Mitchev et al. |
| 6,473,644 B1 | 10/2002 | Terry, Jr. et al. |
| 6,532,388 B1 | 3/2003 | Hill et al. |
| 6,558,708 B1 | 5/2003 | Lin |
| 6,571,127 B1 | 5/2003 | Ben-Haim et al. |
| 6,587,719 B1 | 7/2003 | Barrett et al. |
| 6,591,137 B1 | 7/2003 | Fischell |
| 6,600,956 B2 | 7/2003 | Maschino et al. |
| 6,609,025 B2 | 8/2003 | Barrett et al. |
| 6,610,713 B2 | 8/2003 | Tracey |
| 6,611,715 B1 | 8/2003 | Boveja |
| 6,612,983 B1 | 9/2003 | Marchal |
| 6,622,038 B2 | 9/2003 | Barrett et al. |
| 6,684,105 B2 | 1/2004 | Cohen et al. |
| 6,746,474 B2 | 6/2004 | Saadat |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,895,278 B1 | 5/2005 | Gordon |
| 6,928,320 B2 | 8/2005 | King |
| 6,993,391 B2 | 1/2006 | Flesler et al. |
| 7,054,690 B2 | 5/2006 | Imran |
| 7,072,720 B2 | 7/2006 | Puskas |
| 7,076,307 B2 | 7/2006 | Boveja et al. |
| 7,142,910 B2 | 11/2006 | Puskas |
| 7,158,832 B2 | 1/2007 | Kieval et al. |
| 7,167,750 B2 | 1/2007 | Knudson et al. |
| 7,292,890 B2 | 11/2007 | Whitehurst et al. |
| 7,389,149 B2 | 6/2008 | Rossing et al. |
| 7,444,183 B2 | 10/2008 | Knudson et al. |
| 7,489,969 B2 | 2/2009 | Knudson et al. |
| 7,613,515 B2 | 11/2009 | Knudson |
| 7,620,454 B2 | 11/2009 | Dinsmoor et al. |
| 7,620,455 B2 | 11/2009 | Maschino |
| 7,630,769 B2 | 12/2009 | Knudson |
| 2001/0012828 A1 | 8/2001 | Aoki et al. |
| 2001/0051787 A1 | 12/2001 | Haller et al. |
| 2002/0032468 A1 | 3/2002 | Hill et al. |
| 2002/0052336 A1 | 5/2002 | Yerxa et al. |
| 2002/0055779 A1 | 5/2002 | Andrews |
| 2002/0072780 A1 | 6/2002 | Foley |
| 2002/0087192 A1 | 7/2002 | Barrett et al. |
| 2002/0094962 A1 | 7/2002 | Ashley et al. |
| 2002/0103424 A1 | 8/2002 | Swoyer et al. |
| 2002/0161360 A1 | 10/2002 | Carroll |
| 2002/0198570 A1 | 12/2002 | Puskas |
| 2002/0198571 A1 | 12/2002 | Puskas |
| 2003/0014086 A1 | 1/2003 | Sharma |
| 2003/0018367 A1 | 1/2003 | DiLorenzo |
| 2003/0040785 A1 | 2/2003 | Maschino et al. |
| 2003/0045909 A1 | 3/2003 | Gross et al. |
| 2003/0045914 A1 | 3/2003 | Cohen et al. |
| 2003/0074039 A1 | 4/2003 | Puskas |
| 2003/0135248 A1 | 7/2003 | Stypulkowski |
| 2003/0144709 A1 | 7/2003 | Zabara et al. |
| 2003/0171789 A1 | 9/2003 | Malek et al. |
| 2003/0181958 A1 | 9/2003 | Dobak, III |
| 2003/0181959 A1 | 9/2003 | Dobak, III |
| 2003/0195601 A1 | 10/2003 | Hung et al. |
| 2003/0212440 A1 | 11/2003 | Boveja |
| 2004/0010303 A1 | 1/2004 | Bolea et al. |
| 2004/0019364 A1 | 1/2004 | Kieval et al. |
| 2004/0039425 A1 | 2/2004 | Greenwood-Van Meerveld |
| 2004/0049240 A1 * | 3/2004 | Gerber et al. ................. 607/40 |
| 2004/0059383 A1 | 3/2004 | Puskas |
| 2004/0086531 A1 | 5/2004 | Barron |
| 2004/0089313 A1 | 5/2004 | Utley et al. |
| 2004/0127953 A1 | 7/2004 | Kilgore et al. |
| 2004/0167583 A1 | 8/2004 | Knudson et al. |
| 2004/0172084 A1 | 9/2004 | Knudson et al. |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0176812 A1 | 9/2004 | Knudson et al. |
| 2004/0181178 A1 | 9/2004 | Aldrich et al. |
| 2004/0193229 A1 | 9/2004 | Starkebaum et al. |
| 2004/0236381 A1 | 11/2004 | Dinsmoor et al. |
| 2004/0236382 A1 | 11/2004 | Dinsmoor et al. |
| 2004/0243182 A1 | 12/2004 | Cohen et al. |
| 2004/0249416 A1 | 12/2004 | Yun et al. |
| 2004/0254616 A1 | 12/2004 | Rossing et al. |
| 2005/0038484 A1 | 2/2005 | Knudson et al. |
| 2005/0049655 A1 | 3/2005 | Boveja et al. |
| 2005/0070970 A1 | 3/2005 | Knudson et al. |
| 2005/0070974 A1 | 3/2005 | Knudson et al. |

| | | | |
|---|---|---|---|
| 2005/0075693 A1 | 4/2005 | Toy et al. | |
| 2005/0131485 A1 | 6/2005 | Knudson et al. | |
| 2005/0137644 A1 | 6/2005 | Boveja et al. | |
| 2005/0143378 A1 | 6/2005 | Yun et al. | |
| 2005/0143412 A1 | 6/2005 | Puskas | |
| 2005/0143787 A1 | 6/2005 | Boveja et al. | |
| 2005/0149141 A1 | 7/2005 | Starkebaum | |
| 2005/0149146 A1 | 7/2005 | Boveja et al. | |
| 2005/0149148 A1 | 7/2005 | King | |
| 2005/0203501 A1 | 9/2005 | Aldrich et al. | |
| 2005/0240231 A1 | 10/2005 | Aldrich et al. | |
| 2005/0267542 A1 | 12/2005 | David et al. | |
| 2006/0015151 A1 | 1/2006 | Aldrich | |
| 2006/0030919 A1 | 2/2006 | Mrva et al. | |
| 2006/0036293 A1 | 2/2006 | Whitehurst et al. | |
| 2006/0041277 A1 | 2/2006 | Deem et al. | |
| 2006/0100668 A1 | 5/2006 | Ben-David et al. | |
| 2006/0111626 A1 | 5/2006 | Rossing et al. | |
| 2006/0190053 A1 | 8/2006 | Dobak, III | |
| 2006/0212089 A1 | 9/2006 | Tass | |
| 2006/0247737 A1 | 11/2006 | Olson et al. | |
| 2007/0027484 A1 | 2/2007 | Guzman et al. | |
| 2007/0038260 A1 | 2/2007 | Kieval et al. | |
| 2007/0038261 A1 | 2/2007 | Kieval et al. | |
| 2007/0043400 A1 | 2/2007 | Donders et al. | |
| 2007/0106340 A1 | 5/2007 | Bolea et al. | |
| 2007/0179556 A1 | 8/2007 | Ben Haim et al. | |
| 2008/0004673 A1 | 1/2008 | Rossing et al. | |
| 2008/0046049 A1 | 2/2008 | Skubitz et al. | |
| 2008/0046050 A1 | 2/2008 | Skubitz et al. | |
| 2008/0046054 A1 | 2/2008 | Hjelle et al. | |
| 2008/0082137 A1 | 4/2008 | Kieval et al. | |
| 2008/0177339 A1 | 7/2008 | Bolea et al. | |
| 2008/0177348 A1 | 7/2008 | Bolea et al. | |
| 2008/0177364 A1 | 7/2008 | Bolea et al. | |
| 2008/0177366 A1 | 7/2008 | Bolea et al. | |
| 2008/0183248 A1 | 7/2008 | Rezai et al. | |
| 2009/0275997 A1 | 11/2009 | Faltys et al. | |
| 2009/0306465 A1 | 12/2009 | Dudai | |

FOREIGN PATENT DOCUMENTS

| | | |
|---|---|---|
| EP | 0 076 070 A1 | 4/1983 |
| EP | 1 666 087 A1 | 2/1998 |
| EP | 0 865 800 A2 | 9/1998 |
| EP | 0 896 828 A2 | 2/1999 |
| EP | 1 004 330 A1 | 5/2000 |
| GB | 2 351 911 A | 1/2001 |
| WO | WO 01/41671 A2 | 6/2001 |
| WO | WO 01/43821 A1 | 6/2001 |
| WO | WO 02/26320 A1 | 4/2002 |
| WO | WO 02/065896 | 8/2002 |
| WO | WO 2004/036377 A2 | 4/2004 |
| WO | WO 2004/064918 A1 | 8/2004 |
| WO | WO 2004/082763 A1 | 9/2004 |
| WO | WO 2004/110551 A2 | 12/2004 |
| WO | WO 2009/131639 | 10/2009 |

OTHER PUBLICATIONS

Kilgore, K. et al., "Nerve conduction block utilising high-frequency alternating current," *Medical & Biological Engineering & Computing*, vol. 42, pp. 394-406 (2004).

Kosel, et al., "Beyond the Treatment of Epilepsy: New Applications of Vagus Nerve Stimulation in Psychiatry," *CNS Spectrums*, vol. 8-No. 7, pp. 515-521 (Jul. 2003).

Martin-Portugués et al., "Histopathologic features of the vagus nerve after electrical stimulation in swine," *Histol Histopathol*, vol. 20, pp. 851-856 (2005).

Product Brochure, "ATROSTIM Phrenic Nerve Stimulator," AtroTech Oy, P.O. Box 28, FIN-33721 Tampere, Finland, 2 pages (Jun. 2004).

Roslin, et al., "Vagus nerve stimulation in the treatment of morbid obesity," Ch. 6 to *Vagus Nerve Stimulation, 2nd* Ed., pp. 113-121 (Schlachter et al. ed., Martin Dunitz), 2003.

Amaris et al., "Microprocessor controlled movement of solid colonic content using sequential neural electrical stimulation", *Gut*, 50:475-479 (2002).

Cigaina, "Gastric Pacing As Therapy For Morbid Obesity", *Obesity Surgery*, vol. 12, Supplement, pp. 12S-16S (2002).

D'Argent, "Gastric Electrical Stimulation: Preliminary Results", *Obesity Surgery*, vol. 12, Supplement, pp. 21S-25S (2002).

Koren et al., "Vagus Nerve Stimulation Does Not Lead To Significant Changes In Body Weight In Patients With Epilepsy", Epilepsy & Behavior, vol. 8, pp. 246-249 (2005).

Mintchev, et al., "Electrogastrographic impact of multi-site functional gastric electrical stimulation", *J. of Medical Eng. & Tech.*, vol. 23, No. 1, pp. 5-9 (1999).

Petrofsky, et al., "Impact of Recruitment Order on Electrode Design for Neural Prosthetics of Skeletal Muscle", *Am. J. of Physical Medicine*, vol. 60, No. 5, pp. 243-253 (1981).

Rashev et al., "Microprocessor-Controlled Colonic Peristalsis", *Digestive Diseases and Sciences*, vol. 47, No. 5, pp. 1034-1048 (2002).

Rashev, et al., "Three-dimensional static parametric modeling of phasic colonic contractions for the purpose of microprocessor-controlled functional stimulation", *J. of Medical Eng. & Tech.*, vol. 25, No. 3 pp. 85-96 (2001).

Rösch et al., "Frequency-Dependent Secretion of Pancreatic Amylase, Lipase, Trypsin, and Chymotrypsin During Vagal Stimulation in Rats", *Pancreas*, pp. 499-506 (1990).

Roslin et al., "The Use Of Electrical Stimulation Of The Vagus Nerve To Treat Morbid Obesity", Epilepsy & Behavior, vol. 2, S11-S16 (2001) at p. S13.

Shikora, "'What are the Yanks Doing' The U.S. Experience with Implantable Gastric Stimulation (IGS) for the Treatment of Obesity—Update on the Ongoing Clinical Trials", *Obesity Surgery*, vol. 14, Supplement, S40-S48 (2004).

Solomonow, et al., "Control of Muscle Contractile Force through Indirect High-Frequency Stimulation", *Am. J. of Physical Medicine*, vol. 62, No. 2, pp. 71-82 (1983).

Van Den Honert, et al., "Generation of Unidirectionally Propagated Action Potentials in a Peripheral Nerve by Brief Stimuli", *Science*, vol. 206, pp. 1311-1312.

\* cited by examiner

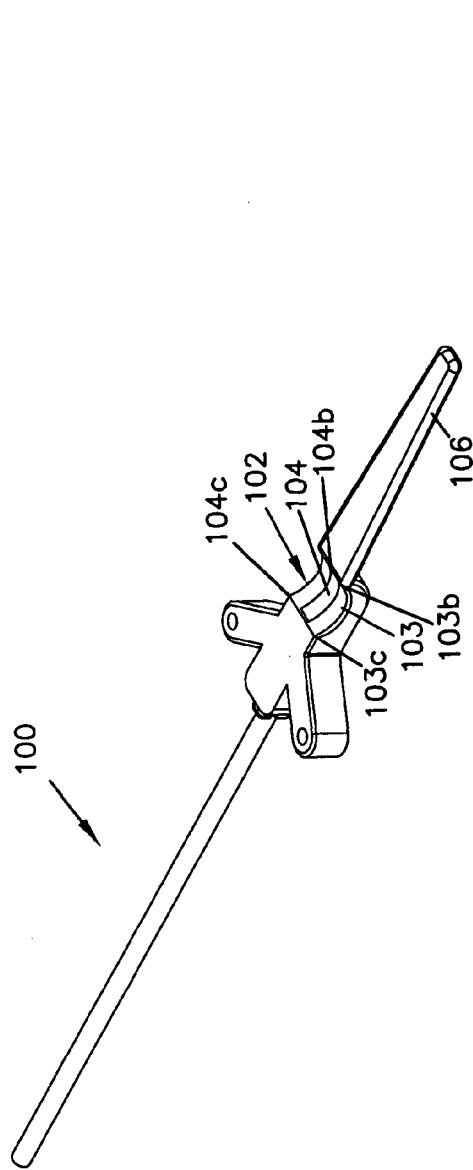
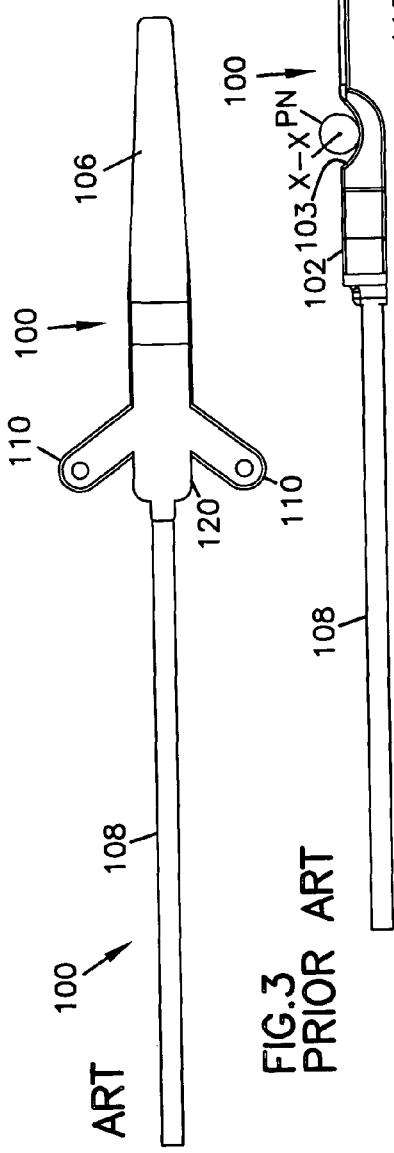
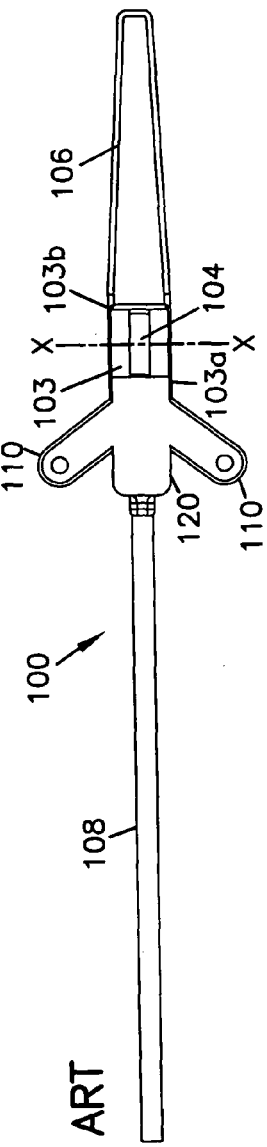
FIG.1 PRIOR ART
FIG.2 PRIOR ART
FIG.3 PRIOR ART
FIG.4 PRIOR ART

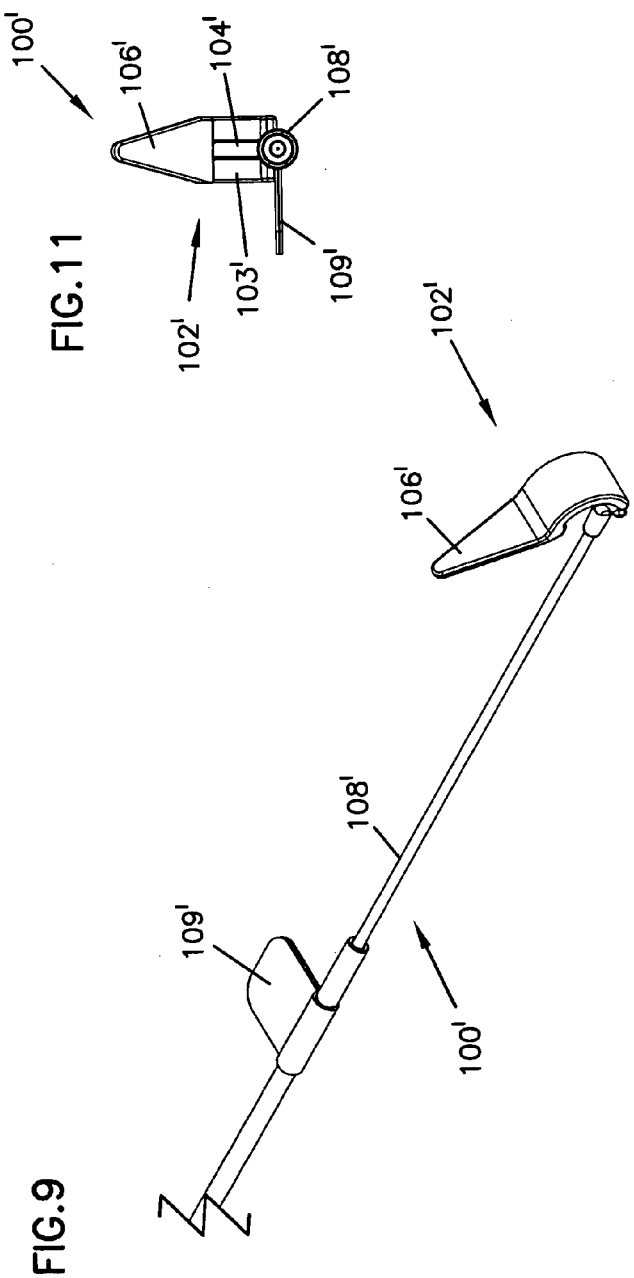
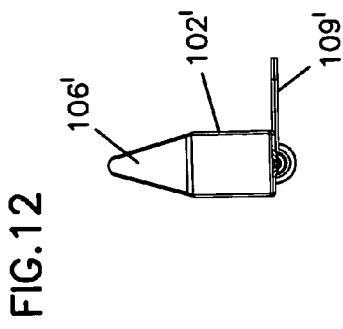
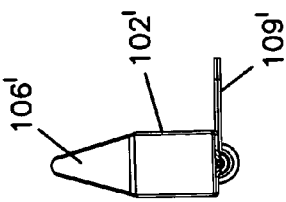
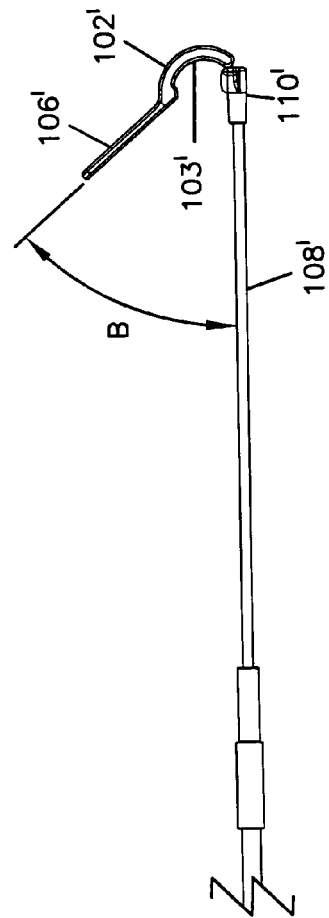
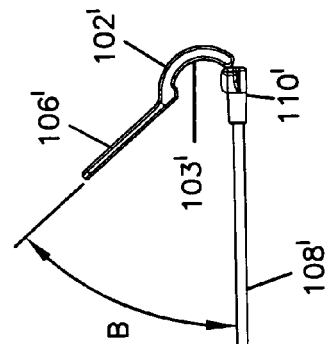

CUSTOM SIZED NEURAL ELECTRODES

I. BACKGROUND OF THE INVENTION

1. Field of the Invention

This invention pertains to electrodes for nerves. More particularly, this invention pertains to such electrodes and signals for placement on the vagus nerve.

2. Description of Related Art

In the prior art, treatments including application of an electrical signal directly to a nerve are known. Examples of such are shown in commonly assigned US Patent Application Publication No. US 2005/0038484 A1 published Feb. 17, 2005. That patent application teaches a number of different therapies which involve applying an electrical signal to a nerve.

An electrical signal applied to a nerve may be a stimulation signal selected to create neural impulses which propagate on the nerve. An electrical signal may also be a blocking signal selected to inhibit the propagation of neural impulses at the point of electrical signal application on the nerve. The '484 patent application publication describes a treatment for obesity (as well as treatments for other disorders) which includes applying a blocking signal to the nerve.

Figure 5:
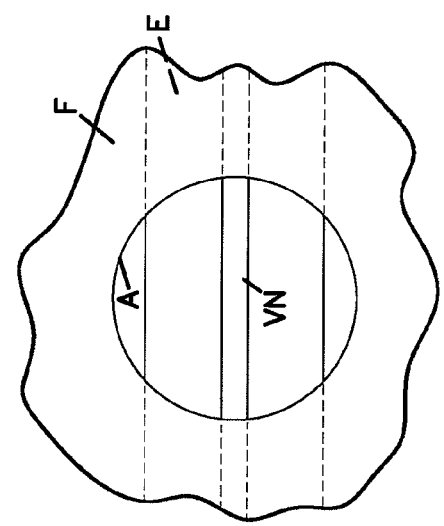
Figure 7:
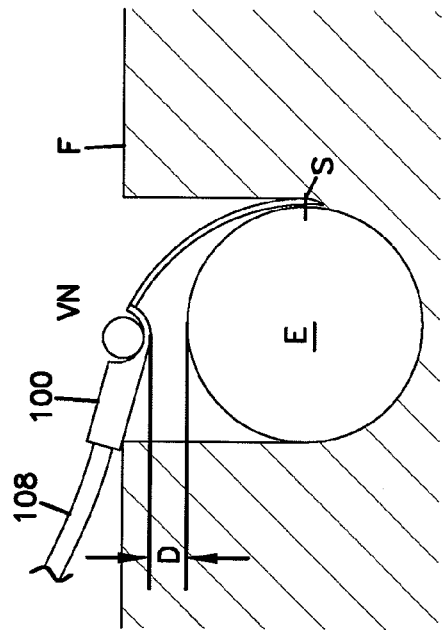

There are many different ways for applying a signal to a nerve. FIG. 7 of the '484 patent application publication shows an apparatus for applying a signal across the esophagus to a vagus nerve lying on outer exterior surface of the esophagus. In the '484 application, the apparatus of FIG. 7 is described in the preferred embodiment for applying a blocking signal to the vagus nerves to down-regulate pancreatic exocrine secretion to treat pancreatitis. FIG. 5 of the '484 application illustrates placement of a band around the esophagus with electrodes on the band overlying the anterior and posterior vagus nerves. As described in the '484 application, blocking signals can be applied to the electrodes to down-regulate vagal activity for the treatment of obesity.

The prior art contains numerous examples of electrodes for placement on nerves and treatments for applying electrical signals to such nerves. For example, U.S. Pat. No. 4,979,511 to Terry, Jr. dated Dec. 25, 1990 teaches an electrode on a helical silicone rubber coil for placement on a cervical vagus nerve for treatment of epilepsy. Also, U.S. Pat. No. 5,215,089 to Baker, Jr. issued Jun. 1, 1993 teaches an electrode for placement on a vagus and U.S. Pat. No. 5,251,634 to Weinberg issued Oct. 12, 1993 and U.S. Pat. No. 5,531,778 to Maschino et al. issued Jul. 2, 1996 and U.S. Pat. No. 6,600,956 to Maschino et al. issued Jul. 29, 2003 teach vagal electrodes.

Other techniques are known for applying signals directly to a nerve. These include patches placed over the nerve with electrodes on the patch positioned to overlie the nerves. In so-called cuff electrodes, a portion of a nerve is dissected to permit a cuff to completely or partially encircle the nerve. An additional optional electrode format is such as that shown in a product brochure called "ATROSTIM Phrenic Nerve Stimulator", AtroTech Oy, P.O. Box 28, Fin-33721, Tampere, Finland (June 2004). The ATROSTIM nerve stimulator includes electrodes on opposite sides of PTFE strips for placement on opposite sides of a phrenic nerve for quad-polar stimulation. Another phrenic nerve electrode is sold by Avery Laboratories, Inc., 61 Mall Drive, Commack, N.Y., USA. The Avery electrode is described in the text of this application. The use of the Avery electrode is described in the website of Avery Laboratories, Inc.

Nerves are fragile. Electrode designs are, in large measure, selected to minimize injury to a nerve. Also, it is important that the electrode be designed for facilitating placement of the electrode on the nerve. Most preferably, the electrode is designed to facilitate placement in a less invasive procedure such as a laparoscopic surgical procedure.

II. SUMMARY OF THE INVENTION

According to a preferred embodiment of the present invention, an apparatus is disclosed for applying a signal to a nerve for the treatment of a disorder. The apparatus includes a main electrode body of biocompatible dielectric material and having a concave upper surface and an opposite lower surface. The concave upper surface curves about an axis and has a curvature sized to receive a nerve within the concave surface with an axis of the nerve substantially parallel to an axis of the concave surface. An electrode contact of electrically conductive material is secured to the main electrode body and has an electrode contact surface exposed on the concave surface. The concave surface terminates at opposite first and second upper ends. The electrode contact has a first end near the first end of the concave surface. A secondary electrode body of biocompatible dielectric material is attached to the first upper end of the concave surface. An electrode lead has an electrical conductor surrounded by a biocompatible insulative coating with both the conductor and the coating flexible relative to a longitudinal axis of the lead. A first end of the lead is secured to the secondary electrode body and with a first end of said conductor electrically connected to said first end of said electrode contact.

III. BRIEF DESCRIPTION OF THE DRAWINGS

Figure 8:
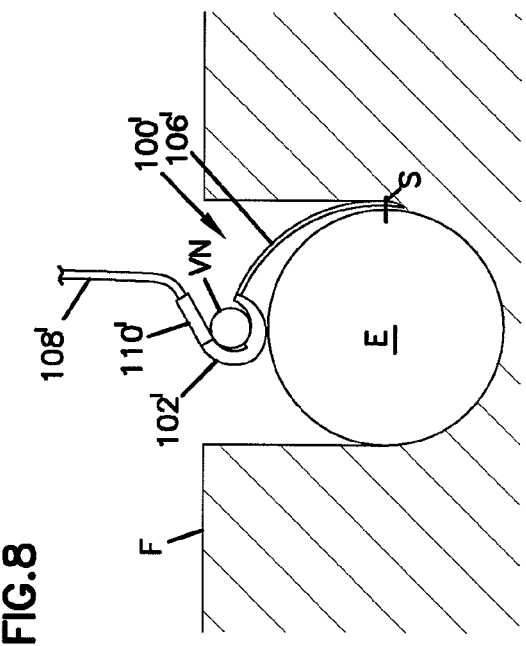
Figure 13:
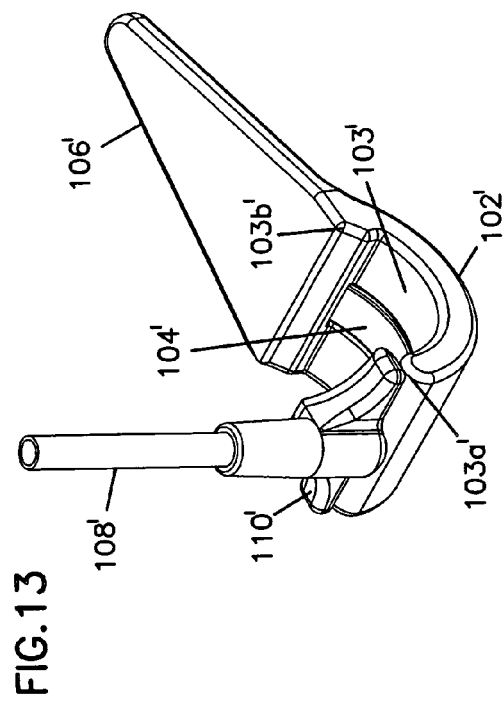
Figure 14:
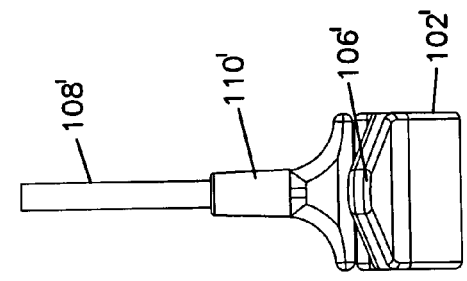
Figure 15:
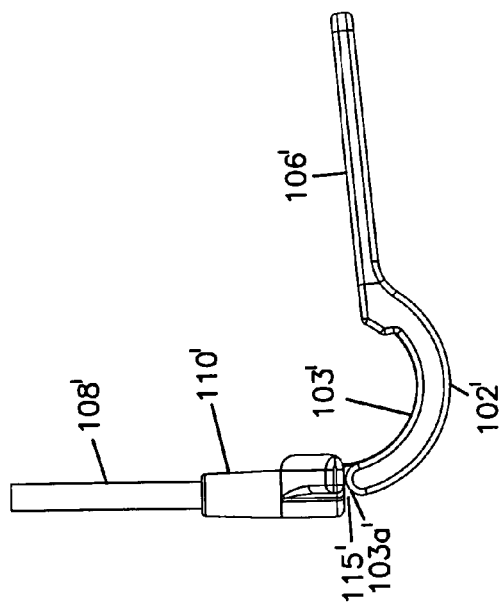
Figure 16:
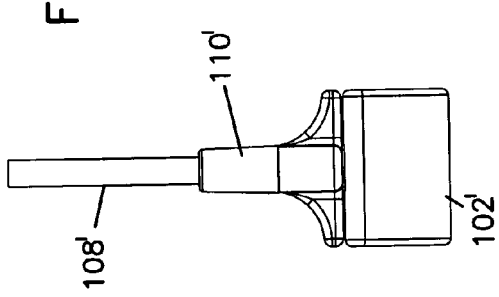
Figure 17:
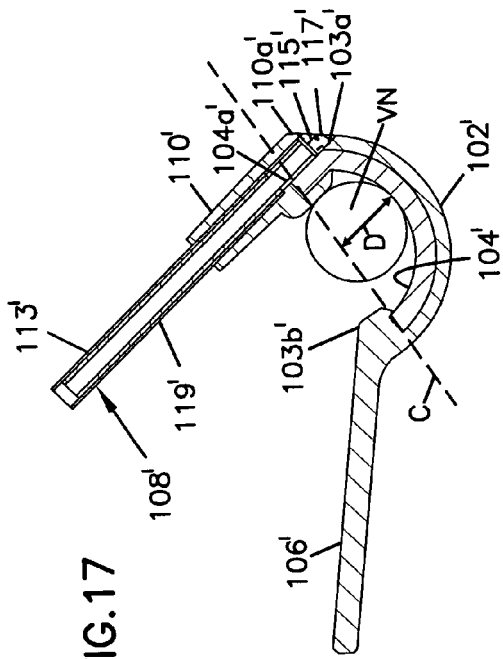

FIG. 1 is a perspective view of a prior art nerve electrode;
FIG. 2 is a bottom plan view of the electrode of FIG. 1;
FIG. 3 is a side elevation view of the electrode of FIG. 1;
FIG. 4 is a top plan view of the electrode of FIG. 1;
FIG. 5 is a top plan view of a vagus nerve on an esophagus and exposed through an access made through a fascia tissue;
FIG. 6 is a side elevation view of the fascia, esophagus, nerve and access of FIG. 5;
FIG. 7 is a cross sectional view of esophagus, nerve and access through fascia with a prior art electrode of FIG. 1 placed on a nerve and illustrating excessive tension on the nerve;
FIG. 8 is the view of FIG. 7 showing an electrode modified according to the present invention;
FIG. 9 is a perspective view of a the electrode according to the present invention and employed in the example of FIG. 8;
FIG. 10 is a side elevation view of the electrode of FIG. 9;
FIG. 11 is a top plan view of the electrode of FIG. 9;
FIG. 12 is a bottom plan view of the electrode of FIG. 9;
FIG. 13 is a perspective view of the electrode of FIG. 13 before final setting of an angle of a lead strain relief molding relative to an electrode body;
FIG. 14 is a front elevation view of the electrode of FIG. 13;
FIG. 15 is a side elevation view of the electrode of FIG. 13;
FIG. 16 is a rear elevation view of the electrode of FIG. 13;
FIG. 17 is side cross-sectional view of the electrode of FIG. 13 after setting the angle of the lead strain relief molding relative to the electrode body;

IV. DESCRIPTION OF THE PREFERRED EMBODIMENT

With reference now to the various drawing figures in which identical elements are numbered identically throughout, a description of the preferred embodiment of the present invention will now be provided. The present invention will be described with reference to an electrode for placement on a nerve. In a preferred embodiment, the electrode is for placement on a vagal nerve such as either or both of the anterior and posterior vagus nerves overlying the esophagus between a diaphragm and a stomach of a patient for the treatment of obesity. It will be appreciated this is a presently preferred embodiment and the present invention has wider applications as will be apparent to those skilled in the art and can be applied to other cranial nerves (such as the vagus) or peripheral nerves. Further, while the preferred embodiment illustrates application of a signal to block the propagation of action potentials along a nerve, the present invention is applicable to signals to stimulate a nerve, inhibit nerve function or only partially block a nerve.

1. Prior Art Electrode

With initial reference to FIGS. 1-4, an electrode such as the aforementioned Avery electrode is shown. The electrode 100 includes a body 102 for receiving a nerve which, in the preferred embodiment of the Avery electrode was a phrenic nerve.

The body 102 has a concave surface 103 with upper edges 103a, 103b. An exposed electrode contact surface area 104 is on the concave surface 103. The contact surface 104 connects to a conductor housed within a highly flexible silicone coated lead 108. The remainder of the electrode 100 is synthetic material such as silicone.

The body 102 has a flexible extension 106 extending from upper edge 103b. On the opposite side of the body 102, the lead 108 extends away from the body 102. The axis of the lead 108 is substantially parallel with the longitudinal axis of the body 102 and parallel with a plane defined by the upper edges 103a, 103b. The body has lugs 110 for suture attachment of the body 102 to anatomical features such as used when placing a phrenic nerve on the electrode. In use, a nerve (such as the phrenic nerve) is placed with the axis of the nerve extending the line designated X-X in FIG. 4. As such the phrenic nerve PN (FIG. 3) resides within the concave surface 103 extending substantially perpendicular to the contact surface 104.

While the electrode 100 of FIGS. 1-4 is proven reliable for use in phrenic nerve stimulation, the electrode 100 has serious disadvantages for use in placement of the electrode on an in situ vagus nerve. The disadvantages of the prior art design of the electrode 100 are illustrated with reference to FIGS. 5-7.

In FIGS. 5-7, an esophagus E is shown with the vagus nerve VN overlying the esophagus. In the drawings, the vagus nerve VN is shown extending substantially parallel to the axis of the esophagus E. In practice, the vagus nerve may be found parallel to the longitudinal axis of the esophagus E or at an angle to the longitudinal axis of the esophagus E. For ease of illustration, only a single vagus nerve VN is shown on the esophagus E. It will be appreciated that beneath the diaphragm, there is both an anterior vagus nerve and a posterior vagus nerve on the esophagus and the present description is applicable to both.

Access to the vagus nerve may be performed through either open surgery or laparoscopic surgery. A tissue layer referred to as the fascia F surrounds the vagus nerve and the esophagus. Accordingly, an access opening is formed by an incision through the fascia to expose the vagus nerve and the esophagus. The access opening is generally indicated at A in FIGS. 5-7.

FIG. 7 illustrates adverse consequences of placement of the electrode 100 on a vagus nerve extending along the esophagus. In FIG. 7, a portion of the nerve VN is dissected away from the esophagus E so that the body of the electrode may be placed between the nerve and the esophagus. The highly flexible extension 106 may be sutured to the esophagus or to any other nearby anatomical structure to prevent migration of the electrode 100. The lead 108 extends upward through the access hole to a source of electrical stimulation (such as in implantable pulse generator or implanted element for receiving trans dermal RF transmission of pulsing signals). The consequence of pulling the lead upwardly (in the view of FIG. 7) can result in a displacement D of the nerve VN from the esophagus E. In FIG. 7, the displacement D is shown exaggerated for ease of illustration. Any such displacement results in undesirable tension on the nerve which can lead to damage to the nerve.

2. Improved Electrode

Referring now to FIGS. 9-17, an improved electrode 100' according to the present invention is shown. The electrode 100' includes a silicone body 102' having a concave surface 103'. An electrode with an exposed contact 104' is exposed on the concave surface 103'. A flexible extension 106' extends longitudinally away from the concave surface 103'. The exposed electrical contact 104' is connected to a lead 108' which terminates at a connector 111' as is conventional. Lugs 109' on the lead 108' facilitate atraumatic grasping of the lead 108'.

The construction of the electrode 100' is best understood with reference to FIGS. 13-17. As best shown in FIG. 17, the body 102' is a concave silicone mold. Centrally positioned on the concave surface 103' is a concave conductor 104' which is imbedded within the silicone material of the body 102' but is exposed on the concave surface 103'.

An upper end 104a' of the electrical contact 104' (shown only in FIG. 17) extends above an upper surface 103a' of the concave surface 103'. An opposite upper end 103b' of the concave surface has the flexible extension 106' extending therefrom. A flexible extension 106' may be simultaneously molded with the body 102' or may be a separate highly flexible silicone material adhered to the upper end 103b'.

The lead 108' is a highly flexible lead which includes a highly flexible coil of conductive material 113' as is conventional in prior art electrode leads. The coil 113' has an outer surface coated with silicone coating 119'.

The upper end 104a' of the contact 104' is electrically connected and bonded to the coil 113' through any suitable means such as welding or the like. A strain relief 110' formed of molded silicone surrounds a lower end of the coil 113' and further surrounds the upper end 104a' of the electrical contact 104'.

A lower back end 110a' of the strain relief 110' is spaced from the upper end 103a' of the body 102'. The spacing defines a gap 115'.

During manufacture, the angle of the lead 113' to the extension 106' may be set by bending the contact at the upper end 104a' causing an enlargement of the gap 115' to that shown in FIG. 17. For example, the angle between the extension 106' and the lead 108' may be set at about 45°. After setting the angle to any desired angle, the gap 115' may be filled with a medical grade adhesive 117' or the like to present an atraumatic surface as well as hold the relative alignment of the extension 106' to the lead 108'.

Where the lead is at 90° to the extension 106' (for example, as shown in FIG. 15), a nerve resting within the concave surface 103' is at risk of moving upwardly or outwardly from the concave surface 103'. Placing the angle at less than 90° presents a barrier above a nerve to prevent or restrict movement of the nerve out of the concave surface without pinching the nerve in a manner to interrupt its blood supply or otherwise causing trauma to the nerve. Following implantation, fibrous tissue or the like may develop around the nerve decreasing possibility of movement of the nerve relative to the electrode body 102'. The present invention can also be practiced with components 110' and 102' being a single-molded part with the angle being fixed and sized for a particular nerve diameter.

With the axis of the lead 108' extending 90° or less relative to the extension 106', the electrode 100' has advantages overcoming the problems previously described with reference to the prior art electrode. These advantages are illustrated in FIG. 8 in which the refined geometry of the electrode 100' results in the lead 108' having a rest state aligned with the access hole A so that the lead is not substantially bent and the body 102' of the electrode is not urged against fascia F which would otherwise cause displacement on the electrode and displacement of the nerve relative to the esophagus.

In a preferred embodiment, the electrode 100' is sized to receive the vagus nerve (anterior or posterior) of an adult human in the region of the diaphragm. While the diameters of such nerves may vary, the electrode 100' preferably can accommodate nerves of diameters ranging from 1 mm to 5 mm. For such nerves, the radius R (FIG. 17) of curvature of the concave electrode 104' is about 3.2 mm and the depth D of about 1.75 mm. The depth is measured as the length of a line normal to the plane C of the upper curved ends of the electrode 104' to the electrode as illustrated in FIG. 17.

With the foregoing detailed description of the present invention, it has been shown how the objects of the invention have been attained in a preferred manner. Modifications and equivalents of disclosed concepts such as those which might readily occur to one skilled in the art, are intended to be included in the scope of the claims which are appended hereto.

What is claimed is:

1. An apparatus for applying a signal to a nerve for the treatment of a disorder, said apparatus comprising:
    a main electrode body of biocompatible dielectric material and having a concave upper surface and an opposite lower surface, said concave upper surface curving about an axis and having a curvature sized to receive a nerve within said concave surface with an axis of said nerve substantially parallel with an axis of said concave surface, said concave surface terminating at opposite first and second upper ends;
    an electrode contact of electrically conductive material secured to said main electrode body and having an electrode contact surface exposed on said concave surface, said electrode contact having a first end extending above said first upper end of said concave surface;
    a flexible extension connected to the main electrode body at the second upper end and extending longitudinally away from the concave surface to form part of a plane extending between said first and second upper ends of said main electrode body;
    a secondary electrode body of biocompatible dielectric material attached to and pivotable relative to said main electrode body at said first upper end of said concave surface, wherein said secondary electrode body is in contact with the first end of the electrode contact, and extends from said first upper end at an angle that is 90° or less relative to the plane extending between said first and second upper ends of said main electrode body and the flexible extension, and can pivot through angles of 90° or less relative to the plane; and
    an electrode lead having an electrical conductor surrounded by a biocompatible insulative coating with both said conductor and said coating flexible relative to a longitudinal axis of said lead, wherein a first end of said lead is secured to said secondary electrode body and a first end of said conductor is electrically connected to said first end of said electrode contact, and the longitudinal axis of the lead extends 90° or less relative to the plane extending between said first and second upper ends of said main electrode body and the flexible extension.

2. An apparatus according to claim 1 wherein said dielectric material of said main body extends axially away from said electrode contact surface on opposite sides thereof.

3. An apparatus according to claim 1 wherein said secondary electrode body is connected to said first upper end by direct connection of said secondary electrode body to said first end of said electrode contact.

4. An apparatus according to claim 3 further comprising a filler material between said main electrode body and said secondary electrode body to fix an angle between said main electrode body and said secondary electrode body.

5. The apparatus of claim 1, wherein the main body electrode accommodates nerves of diameters from 1 to 5 mm.

6. The apparatus of claim 1, wherein the main body electrode accommodates a vagus nerve.

\* \* \* \* \*